US011116781B2

(12) United States Patent
Jeong et al.

(10) Patent No.: US 11,116,781 B2
(45) Date of Patent: Sep. 14, 2021

(54) COMPOSITION, CONTAINING LOGANIN OR A DERIVATIVE THEREOF AS AN ACTIVE INGREDIENT FOR PREVENTING, REMEDYING, OR TREATING FEMALE CLIMACTERIC SYNDROME (71) Applicant: NINE B CO., LTD., Daejeon (KR)

(72) Inventors: Seon-Yong Jeong, Yongin-si (KR); Eun Kuk Park, Suwon-si (KR); Mun-Chang Kim, Changwon-si (KR); Jeong Hyun Kim, Suwon-si (KR)

(73) Assignee: NINE B CO., LTD., Daejeon (KR)

( * ) Notice: Subject to any disclaimer, the term of this patent is extended or adjusted under 35 U.S.C. 154(b) by 0 days.

(21) Appl. No.: 16/069,522

(22) PCT Filed: Jan. 13, 2017

(86) PCT No.: PCT/KR2017/000438
§ 371 (c)(1),
(2) Date: Jul. 12, 2018

(87) PCT Pub. No.: WO2017/123030
PCT Pub. Date: Jul. 20, 2017

(65) Prior Publication Data
US 2019/0000869 A1    Jan. 3, 2019

(30) Foreign Application Priority Data

Jan. 13, 2016  (KR) .................. 10-2016-0004169

(51) Int. Cl.
*A61K 31/7048*    (2006.01)
*A61P 5/30*    (2006.01)
*A23L 33/10*    (2016.01)
*A61K 36/56*    (2006.01)

(52) U.S. Cl.
CPC .......... *A61K 31/7048* (2013.01); *A23L 33/10* (2016.08); *A61K 36/56* (2013.01); *A61P 5/30* (2018.01); *A23V 2002/00* (2013.01); *Y02A 50/30* (2018.01)

(58) Field of Classification Search
CPC ........ A61K 31/7048; A61K 36/56; A61P 5/30
See application file for complete search history.

(56) References Cited

FOREIGN PATENT DOCUMENTS

| CN | 1876096 A | 12/2006 |
|---|---|---|
| CN | 101085146 A | 12/2007 |
| CN | 101658626 A | 3/2010 |
| CN | 101757410 A | 6/2010 |
| CN | 102264362 A | 11/2011 |
| CN | 102824400 A | 12/2012 |
| CN | 103110651 A | 5/2013 |
| CN | 104706704 A | 6/2015 |
| CN | 104887693 A | 9/2015 |
| KR | 10-1225566 B1 | 1/2013 |
| KR | 10-2015-0037208 A | 4/2015 |
| WO | 89/12626 A1 | 12/1989 |
| WO | 2010/074361 A1 | 7/2010 |

OTHER PUBLICATIONS

Carmen Recio, M. et al., Planta Med, "Structural Considerations on the Iridoids as Anti-Inflammatory Agents", 1994, vol. 60, pp. 232-234 (Year: 1994).*
Jia-qing, Z. et al., CJIM, "Changes of Leucocytic Estrogen Receptor Levels in Patients with Climacteric Syndrome and the Therapeutic Effects of Liuwei Dihuang Pills", 1995, vol. 1, No. 1, pp. 9-12 (Year: 1995).*
Kwee, S.H. et al., Maturitas, "The effect of Chinese herbal medicines (CHM) on menopausal symptoms compared to hormone replacement therapy (HRT) and placebo", 2007, vol. 58, pp. 83-90 (Year: 2007).*
Merriam-Webster Online Dictionary "derivative"; last viewed 2009; available at http://www.merriam-webster.com/dictionary/derivative (Year: 2009).*
Xie, Baogang et al., Journal of Pharmaceutical and Biomedical Analysis, "An approach based on HPLC-fingerprint and chemometrics to quality consistency evaluation of Liuwei Dihuang Pills produced by different manufacturers", 2008, vol. 48, pp. 1261-1266 (Year: 2008).*
Xie, Baogang et al., Phytotherapy Research, "Enhanced Estrogenic Activity of Soybean Isoflavones by Coadministration of Liuwei Dihuang Pills in Ovariectomized Rats", Mar. 2015, vol. 29, pp. 1054-1061 (Year: 2015).*
Dubey, R. K. et al., Hypertension, "Hormone Replacement Therapy and Cardiovascular Disease: What went wrong and where do we go from here?", 2004, vol. 44, pp. 789-795 (Year: 2004).*
Kwon, S.-H. et al., European Journal of Pharmacology, "Loganin improves learning and memory impairments induced by scopolamine in mice", 2009, vol. 619, pp. 44-49 (Year: 2009).*
Ortmann, O. et al., Dtsch Arztebl Int., "The Treatment of Climacteric Symptoms", 2012, vol. 109, No. 17, pp. 316-324 (Year: 2012).*
"Prevent" definition, Princeton University "About WordNet." WordNet. Princeton University. 2010 (Year: 2010).*
Xu, M. et al., Sleep Medicine, "Comparison of subjective and objective sleep quality in menopausal and non-menopausal women with insomnia", 2011, vol. 12, pp. 65-69 (Year: 2011).*

(Continued)

*Primary Examiner* — Bahar Craigo
(74) *Attorney, Agent, or Firm* — Revolution IP, PLLC (57) ABSTRACT

A pharmaceutical composition for preventing or treating female climacteric syndromes comprising Loganin which increases the concentration of estradiol (17β-estradiol, E2) in the blood of a menopausal mouse model and has shown efficacies such as an increase in the estrogen receptor alpha expression in the uterus, which remedies uterine contraction and degeneration, and decreases in the accumulation and the size of adipocytes in liver and the abdominal adipose tissues and the liver and weight loss, a derivative thereof or a pharmaceutically acceptable salt thereof as an active ingredient.

4 Claims, 12 Drawing Sheets

(56) References Cited

OTHER PUBLICATIONS

Yamabe, N. et al., European Journal of Pharmacology, "Evaluation of loganin, iridoid glycoside from Corni Fructus, on hepatic and renal glucolipotoxicity and inflammation in type 2 diabetic db/db mice", 2010, vol. 648, pp. 179-187 (Year: 2010).*

International Search Report for PCT/KR2017/000438 dated Apr. 18, 2017 from Korean Intellectual Property Office.

Li, M. et al., "The Pharmacological Effects of Morroniside and Loganin Isolated from Liuweidihuang Wan, on MC3T3-E1 Cells", Molecules 2010, vol. 15, pp. 7403-7414.

Dongwoodang Pharmacy Co., Ltd., "Development of functional foods having an effect on prevention and improvement of osteoporosis via regulating the key gene expression associated with bone metabolism", Research Yeporter, 2015, Publications Registration No. 11-1543000-000815-01.

Nux vomica(Strychnos nux-vomica)—Erma's Nutrition Center.

MF Bordet et al., "Treating hot flushes in menopausal women with homeopathic treatment—Results of an observational study", Published 2008, Homeopathy : the journal of the Faculty of Homeopathy.

* cited by examiner

COMPOSITION, CONTAINING LOGANIN OR A DERIVATIVE THEREOF AS AN ACTIVE INGREDIENT FOR PREVENTING, REMEDYING, OR TREATING FEMALE CLIMACTERIC SYNDROME

TECHNICAL FIELD

The present invention relates to a composition for preventing, improving or treating female climacteric syndromes, which contains Loganin, a derivative thereof or a pharmaceutically acceptable salt thereof as an active ingredient.

BACKGROUND ART

Estrogen, a representative hormone that symbolizes female, is an important female hormone that regulates the lifespan of women through menstruation, pregnancy and menopause. Estrogen is well known as the female hormone which is mainly secreted from follicles, corpus luteum and placenta in the ovaries and is collective name for estrogen (E1), estradiol (E2) and estriol (E3). Among them, estradiol (E2) shows the strongest activity among estrogens.

Sex hormones of women are mainly associated with reproductive activities, and secretion thereof is regulated by menstrual cycle. These are controlled by follicle stimulating hormone (FSH). When estrogen is secreted, feedback action reduces follicle stimulating hormone secretion and increases the secretion of luteinizing hormone (LH). The estrogen used in the body is changed into a proper structure for being released from the liver and then excreted through the urine. In addition to estrogen, progesterone is also regulated by luteinizing hormone, and is closely related to estrogen, so proper balance of estrogen and progesterone is important.

Figure 1:
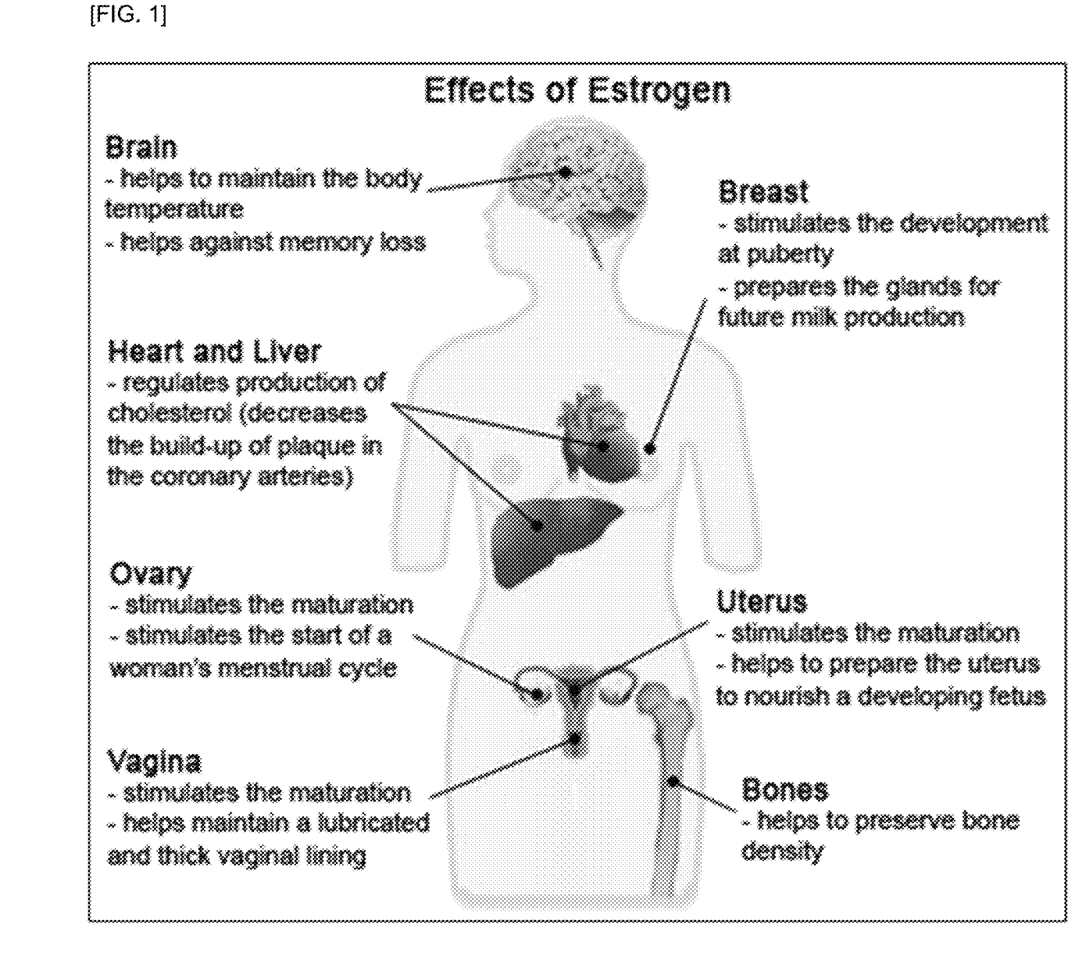
FIG. 1 shows the effect of estrogen on the body.

Estrogen affects a wide range of tissues and organs, ranging from the brain to the liver and bone. Estrogen is particularly needed to maintain flexibility and normal state of the uterus, urinary, breast, skin, and blood vessels (FIG. 1).

Figure 2:
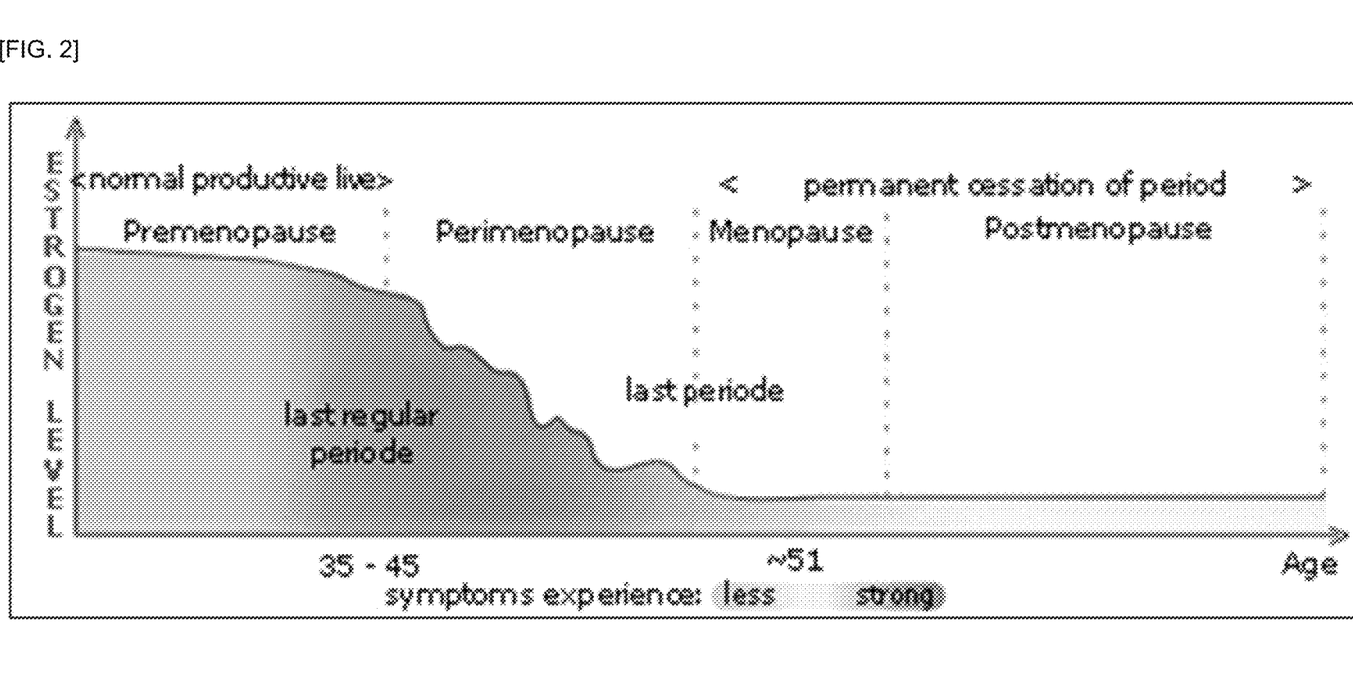
FIG. 2 shows the level of estrogen in a woman's lifetime.

Women's climacterium, also called menopause, refers to the period of transition from maturity to old age based on the function of the ovaries. The climacteric age varies according to physical condition, nutritional status, and number of birth deliveries, but statistically it is around 50 years old. The menopause tends to be delayed slightly due to the prolongation of life expectancy. The onset of climacterium begins from the period of perimenopause, which the amount of estrogen begins to decrease. During menopause, the production of estrogen and progesterone is very low and menstruation is completely stopped. Also, the postmenopausal period begins about 12 months after the menstration is completely stopped. (FIG. 2).

When the climacterium begins, the female hormones secreted from the ovaries are reduced by hypofunction and malfunction of the function of the ovaries, which result various symptoms, such as, irregular cycle, period and amount of menstruation, the symptoms of facial flushing on mainly face and upper body, sweating and heart beating, atrophy of genital organ such as vulva getting dried and decrease in vaginal mucus secretion, increase in frequency of urine and pain during urination. In addition, symptoms such as dizziness, tinnitus, hypertension, digestive disorders, headache, sleeping disorders, memory loss, cognitive impairment, mood swings and depression may occur. Furthermore, during menopause, calcium is leached from the bone and weakens the bones, which can cause back pain or other bone related pain and the bone can easily be fractured. Because estrogen is involved in stimulating and developing the muscles in the uterus, estrogen receptors are remarkably reduced in uterine tissue cells due to estrogen decrease.

Figure 3:
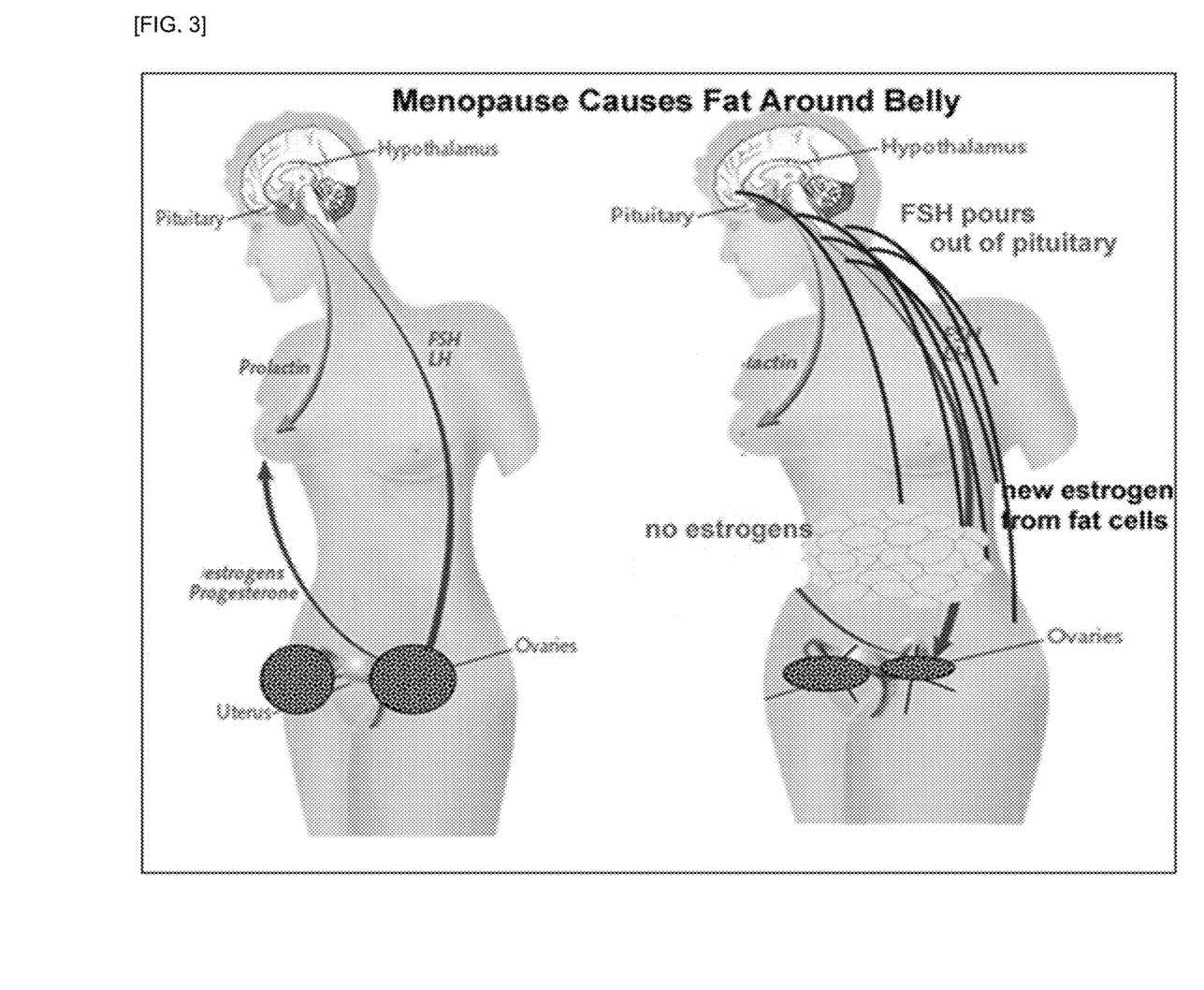
FIG. 3 shows the adipocyte accumulation process in abdominal adipose tissue to offset the estrogen deficiency.

The estrogen receptor is activated by estradiol (17β-estradiol, E2) and has two classes of estrogen receptor alpha and beta. In the uterus, the estrogen receptor alpha plays a more important role than the estrogen receptor beta, and during climacterium, a marked reduction in the estrogen receptor alpha causes contraction and degeneration of the uterus. It also produces new estrogen from adipocyte in adipose tissue to offset the estrogen deficiency. During this process, more fat cells are produced and can cause abdominal obesity (FIG. 3).

Figure 4:
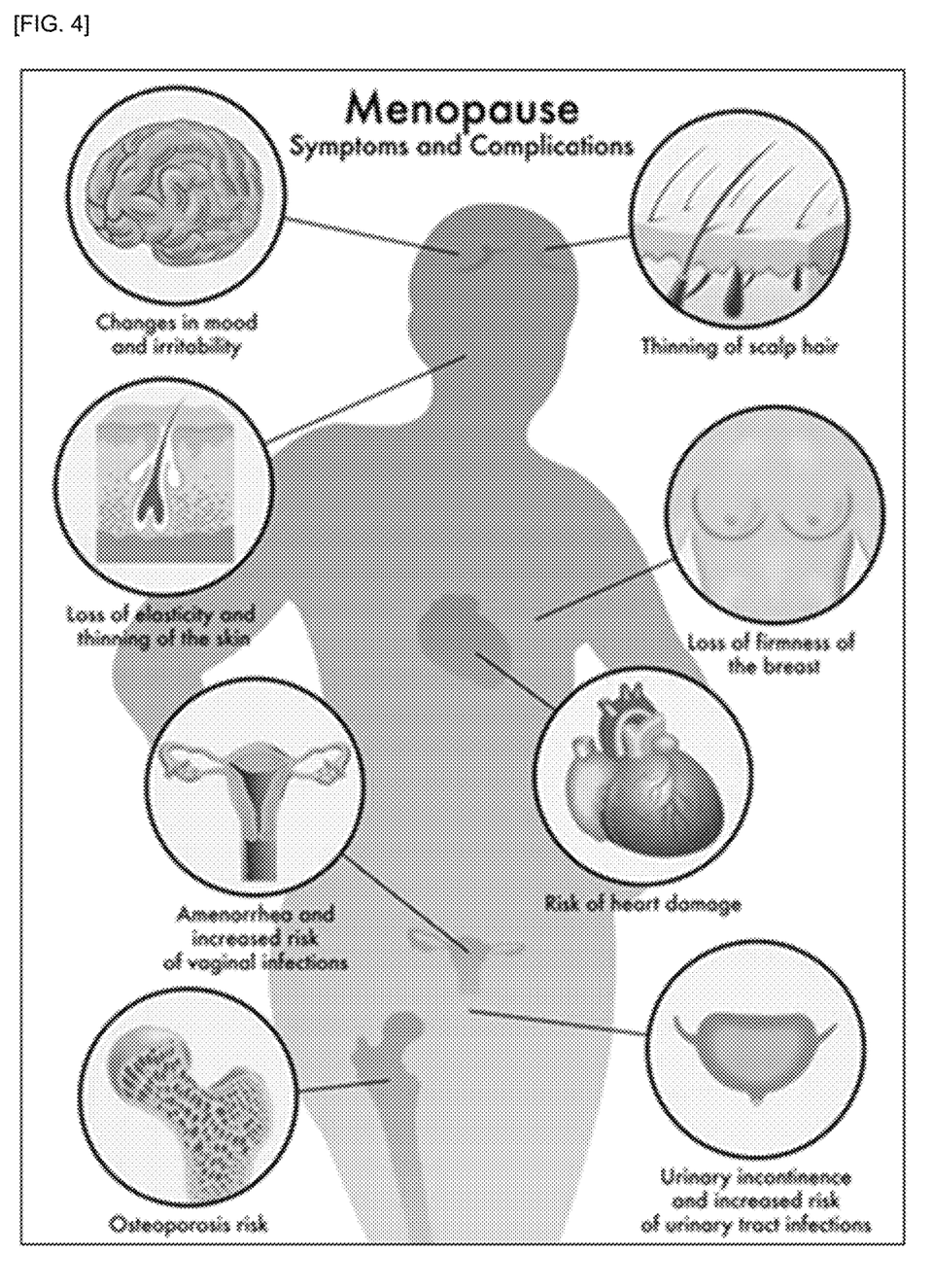
FIG. 4 shows the types and symptoms of female climacteric syndromes.

The types and degree of climacteric symptoms vary widely from mild enough for daily life to severe enough to lie in sickbed according to individual differences (FIG. 4). About 30% of menopausal women are known to have severe symptoms and to be treated. As to the treatment, female hormone treatments are used, but there are reports of side effects and there are some cases where bone density is continuously reduced and treatment for osteoporosis is needed. On the other hand, health functional foods such as cynanchi wilfordii radix complex extract and pomegranate concentrate or calcium, vitamin D and isoflavone good for bone health are also used for alleviating menopausal symptoms but their effects are limited. Therefore, there is a need for development of a pharmaceutical formulation or health functional food for the preventing, improving and treating women's climacteric symptoms more effectively.

DISCLOSURE

Technical Problem

The present invention provides a composition for preventing, improving or treating female climacteric syndromes, which contains Loganin, a derivative thereof or a pharmaceutically acceptable salt thereof as an active ingredient, and more particularly, provides a composition for preventing, improving and treating the decrease of estrogen hormone, weight gain, fat accumulation in liver and abdominal adipose tissue, and fat cell size increase.

Technical Solution

The present invention provides a pharmaceutical composition for preventing or treating female climacteric syndromes, which contains Loganin, a derivative thereof or a pharmaceutically acceptable salt thereof as an active ingredient.

In addition, the present invention provides a health food composition for preventing or improving female climacteric syndromes, which contains Loganin, a derivative thereof or a pharmaceutically acceptable salt thereof as an active ingredient.

Advantageous Effects

The present invention relates to a composition for preventing, improving or treating female climacteric syndromes, which contains Loganin, a derivative thereof or a pharmaceutically acceptable salt thereof as an active ingredient. The Loganin of the present invention increases the blood concentration of estradiol (17β-estradiol, E2) in the menopausal mouse model, increases the expression level of estrogen receptor alpha in the uterus, improves uterine contraction and degeneration, and exhibits effect for reduction of fat cell accumulation and size in liver and abdominal adipose tissue and weight loss. Loganin has the effect of improving the estrogen reduction in menopausal women, increases of body weight, fat accumulation and fat cell size increase in the liver and abdominal adipose tissue. Accordingly, the Loganin of the present invention and the composition containing the same as an active ingredient are expected to be used as a pharmaceutical preparation for preventing and improving symptoms related to climacteric syndromes.

BEST MODE

In vivo efficacy of Loganin, a sole compound that is effective in reducing estrogen hormone and improving the resulting weight gain and fat accumulation and fat cell size increase in liver and abdominal adipose tissue in climacteric women.

The present invention provides a pharmaceutical composition for preventing or treating female climacteric syndromes, which contains Loganin, a derivative thereof or a pharmaceutically acceptable salt thereof as an active ingredient.

Specially, the female climacteric syndrome may be caused by a decrease in estrogen secretion and the decrease in estrogen secretion may reduce an expression level of estrogen receptor alpha in uterine tissue cells and increase insulin and leptin protein in the blood.

Particularly, the female climacteric syndrome consists of hot flush, sweating, insomnia, nervousness, depression, dizziness, concentration deficiency, short term memory impairment, anxiety, memory loss, palpitations, myalgia, joint pain, skin dryness, vaginal dryness, vaginal atrophy, lower urinary tract atrophy, vaginitis, uterine atrophy, cystitis, dysentery, rubella, abdominal obesity, hyperlipidemia, arteriosclerosis or fatty liver, but is not limited thereto.

The Loganin of the present invention is represented by the Chemical Formula 1 and the molecular formula is $C_{17}H_{26}O_{10}$.

<Chemical Formula 1>

In the present invention, the pharmaceutically acceptable salt may be an acid addition salt produced with an organic acid selected from the group consisting of oxalic acid, maleic acid, fumaric acid, malic acid, tartaric acid, citric acid and benzoic acid, or an inorganic acid selected from the group consisting of hydrochloric acid, sulfuric acid, phosphoric acid and hydrobromic acid.

In case that the composition of the present invention is a pharmaceutical composition, the pharmaceutical composition may be formulated into a cream, a gel, a patch, a spray, an ointment, a plaster, a lotion, a liniment, a pasta agent and a cataplasma agent, etc. Meanwhile, the pharmaceutical composition may include a pharmaceutically acceptable carrier in addition to the Loganin and the above pharmaceutically acceptable carriers are those conventionally used in pharmaceutical preparations such as lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, etc., but are not limited thereto. In addition, the pharmaceutical composition may further include a lubricant, a wetting agent, a sweetener, a flavoring agent, an emulsifying agent, a suspending agent, a preservative, etc. as an additive.

The administration method of the pharmaceutical composition may be determined according to the severity of the symptoms of climacteric syndrome and generally, topical administration is preferred. The dosage of the active ingredient in the pharmaceutical composition may vary depending on the route of administration, the severity of the disease, the age, sex and weight of the patient and may be administered once to several times per day.

Also, the present invention provides a health food composition for preventing or improving female climacteric syndromes, which contains Loganin, a derivative thereof or a pharmaceutically acceptable salt thereof as an active ingredient.

The health food composition may be provided in the form of a powder, a granule, a tablet, a capsule, a syrup, a beverage or a pill, and the health food composition may contain other food or food additives in addition to the active ingredient Loganin and can be suitably used according to a conventional method. The amount of the active ingredient to be mixed can be appropriately determined according to its use purpose, for example, prevention, health or therapeutic treatment.

The effective dose of Loganin contained in the above health food composition may be used in accordance with the effective dose of the pharmaceutical composition, but in the case of long-term ingestion for health and hygiene purposes or controlling health, and the active ingredient may be used in an amount of the above range and less and it is clear that the active ingredient can be used in an amount of the above range and more because there is no safety problem.

There is no particular limitation on the kind of the health food and examples thereof include meat, sausage, bread, chocolate, candy, snack, confectionery, pizza, ramen, other noodles, gums, dairy products including ice cream, various soup, beverages, tea, drinks, alcoholic beverages and vitamin complexes, etc.

Hereinafter, examples of the present invention will be described in detail as to the present invention. The present invention may, however, be embodied in many different forms and should not be limited to the embodiments set forth herein in order to clearly illustrate the present invention for those skilled in the art to which the present invention pertains.

<Example 1> Outline of Experiment of Climacteric Animal Model

Figure 5:
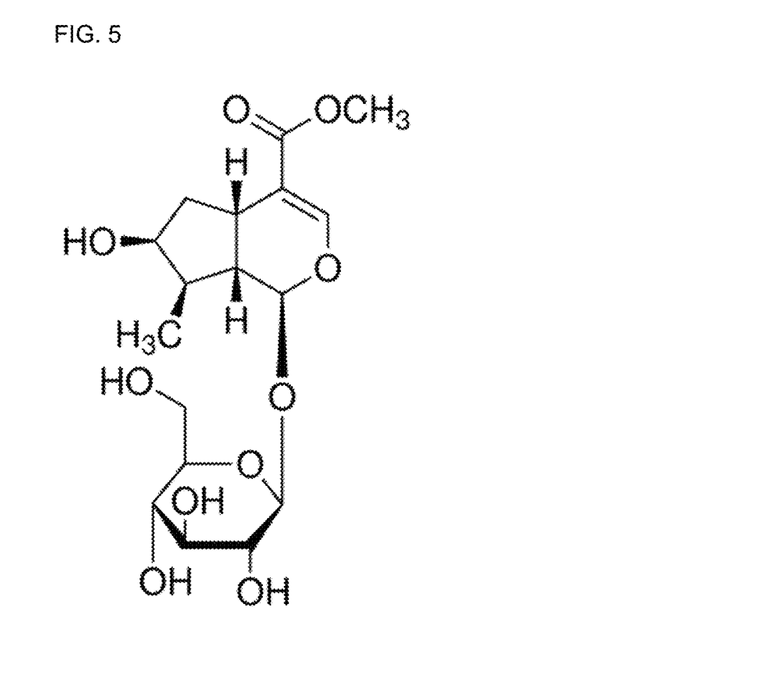
FIG. 5 shows the chemical formula of Loganin.

The single test compound used in animal experiments in the present invention is Loganin. Loganin is an iridoid glycosides, which is a name induced from Loganiaceae and its chemical formula is $C_{17}H_{26}O_{10}$ (FIG. 5). Loganin is a naturally occurring single compound, which is abundant in nux vomica and *Cornus officinalis*.

A 10-week-old ovariectomized ddY female mouse (OVX mouse) was used as a climacteric animal model to evaluate the in vivo efficacy of Loganin (ovariectomy after 8 weeks and 2 weeks of additional feeding for recovering conditions). Sham mouse group cut the abdomen open without ovariectomy (normal control group) was used as control group, and OVX mouse group in which physiological saline alone was administered to ovariectomized mice (negative control group) and $SrCl_2$ mouse group in which a single compound, strontium chloride ($SrCl_2$), was orally injected at a dose of 10 mg/kg/day (comparison group of non-efficacious compound administration) were used. 10-week-old Sham-operated and ovariectomized ddY female mice were purchased from Central Laboratory Animals Co. and transferred to a clean animal breeding area after a 1-week purifying period in the quarantine room of Experimental Animal Center in Ajou University. The weight of each mouse was measured and group separation was performed so that there was no statistically significant weight difference between the experimental groups. For the experiment, a test solution of Loganin was prepared as an aqueous solution and in order to bring in the laboratory animal center, a sterilization operation was carried out by irradiating with a gamma ray by a radiation irradiation professional company, Soyagreentec Co., Ltd. In the test group, Loganin was orally injected at a dose of 10 mg/kg/day for 12 weeks and blood estrogen level, estrogen receptor alpha expression level in uterus tissue, uterine size, body weight, and fat cell size of liver and abdominal adipose tissue were measured and analyzed.

Figure 6A:
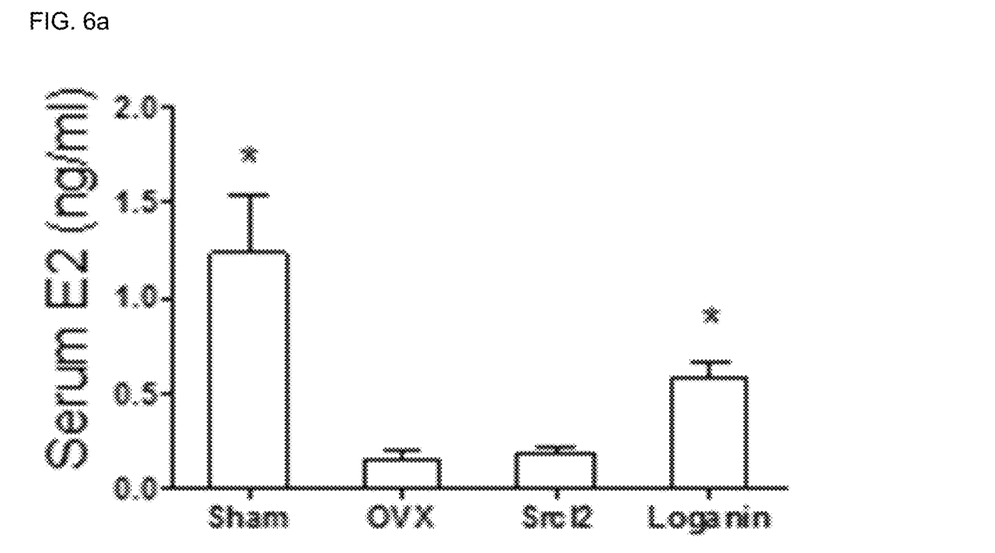
FIG. 6a shows the results of measuring female hormone estradiol (E2) after 12 weeks of administration of Loganin of 10 mg/kg/day to climacteric mouse model (ovariectomized-mouse) followed by separating serum from blood of mice, indicating that Loganin is significantly effective in inhibiting female hormone reduction of climacterium.
Figure 6B:
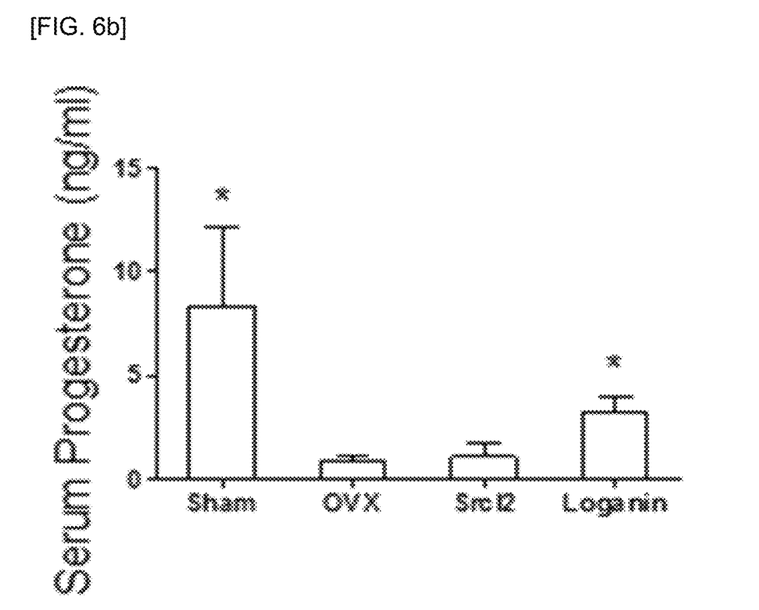
FIG. 6b shows the results of measuring female hormone progesterone after 12 weeks of administration of Loganin of 10 mg/kg/day to climacteric mouse model (ovariectomized-mouse) followed by separating serum from blood of mice, indicating that Loganin is significantly effective in inhibiting female hormone reduction of climacterium.
Figure 6C:
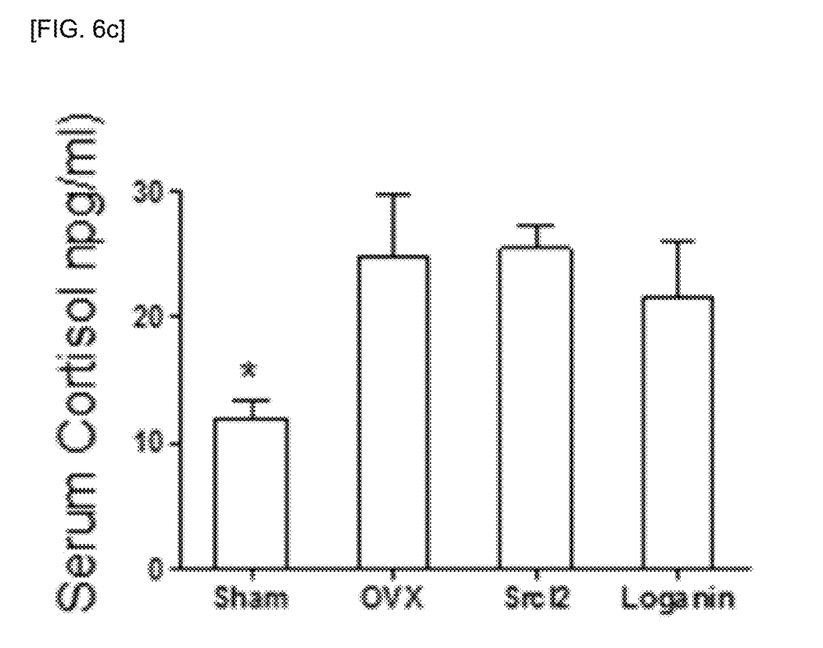
FIG. 6c shows the results of measuring the amount of cortisol, which is a stress hormone secreted from adrenal gland, in the blood.

<Example 2> Improvement Effect of Blood Estrogen Reduction of Loganin in a Female Model of Menopausal Period An ordinary female climacteric symptom results in a significant reduction in female hormones, i.e. estrogen and progesterone. The amount of estradiol (17β-estradiol, E2)

and progesterone which are estrogen in the blood was measured by ELISA after 12 weeks of administration of Loganin to female climacteric mouse model. When compared to normal Sham mice without ovariectomy, the female hormones, estradiol (FIG. 6a) and progesterone (FIG. 6b), were significantly decreased in ovariectomized OVX mouse. A comparison group of non-efficacious compound administration, $SrCl_2$ mouse has no difference with OVX mouse. However, in the Loganin-administered group, the decrease level of estradiol and progesterone in the blood were significantly inhibited (FIGS. 6a and 6b). Statistical analysis also showed significance of efficacy (*: $p<0.05$ vs. OVX negative control). To confirm the stress level of each mouse group, the amount of cortisol, which is a stress hormone secreted from adrenal gland, in the blood was higher than that of Sham mouse group, however, there is no significant difference between OVX mouse group, $SrCl_2$ mouse group and Loganin-administered mouse group (FIG. 6c).

Figure 7A:
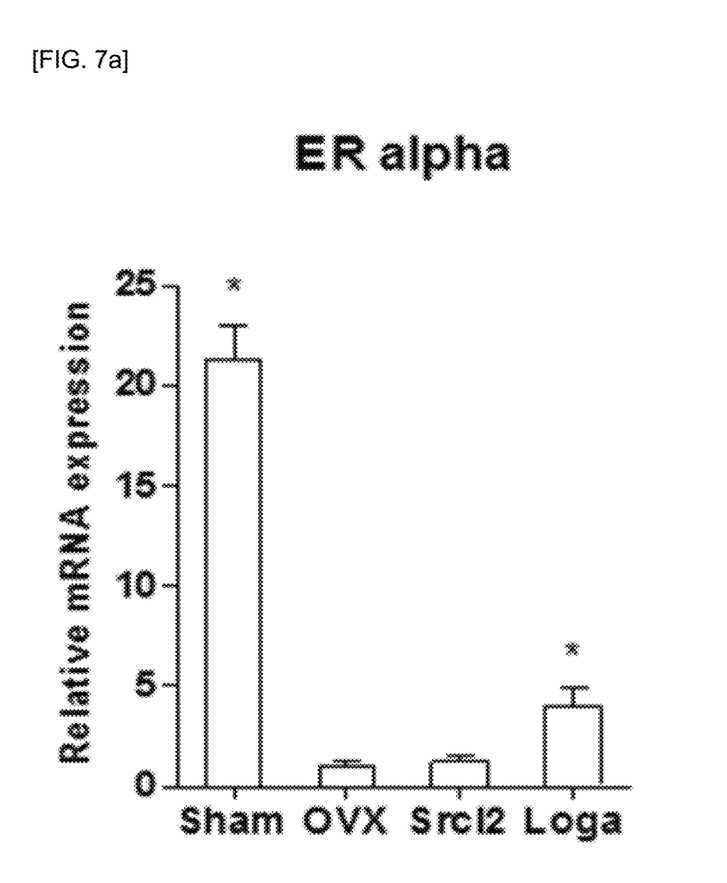
FIG. 7a shows the results of measuring the mRNA expression level of the estrogen receptor alpha gene after 12 weeks of administration of Loganin of 10 mg/kg/day to climacteric mouse model followed by extirpating uterus, indicating that Loganin is significantly effective in inhibiting the decrease in estrogen receptor alpha expression level in uterine tissue cells by the climacterium.
Figure 7B:
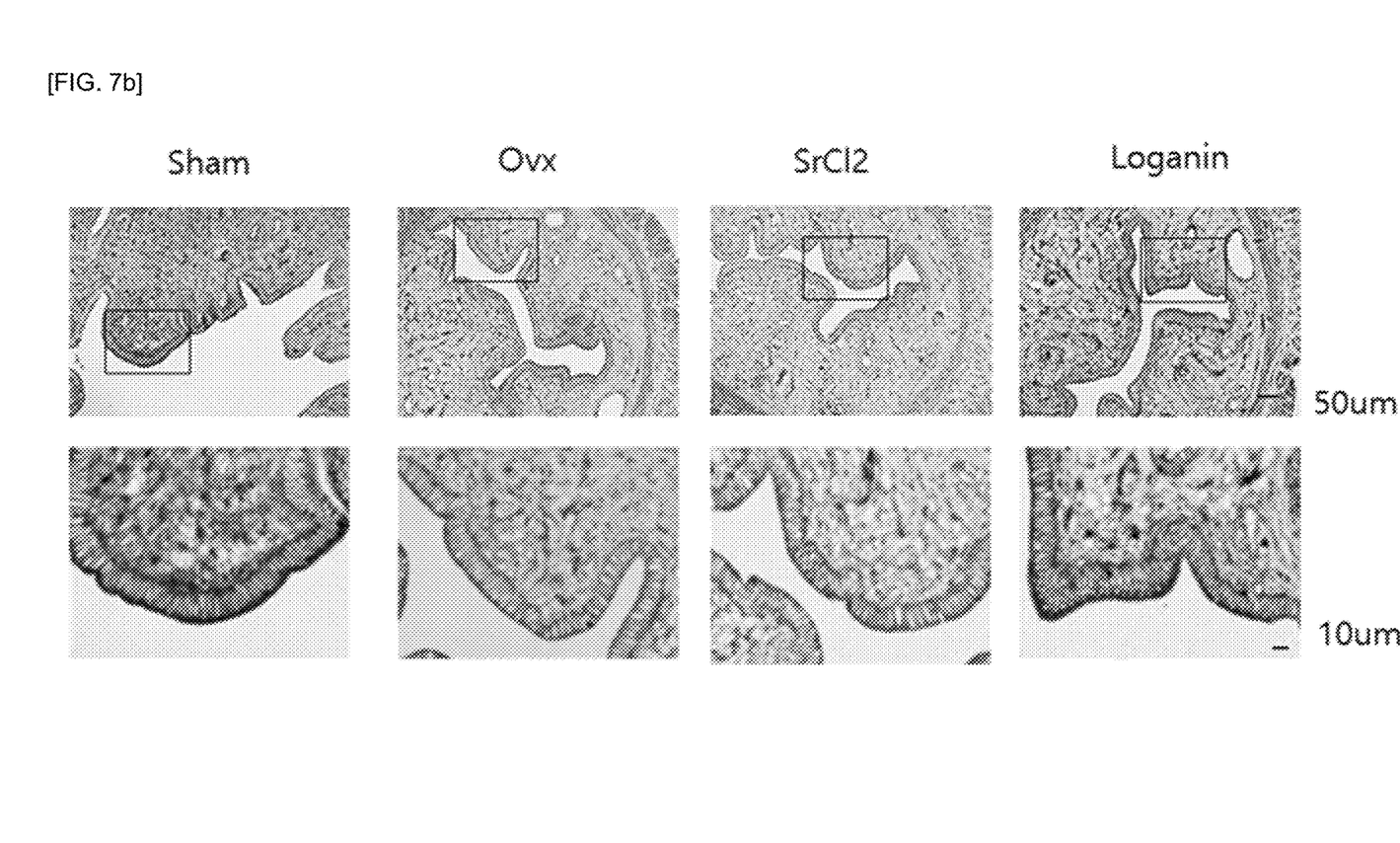
FIG. 7b shows the results of measuring the estrogen receptor alpha protein expression level by immunohistochemistry of section of the uterus after 12 weeks of administration of Loganin of 10 mg/kg/day to climacteric mouse model followed by extirpating uterus, indicating that Loganin is significantly effective in inhibiting the decrease in estrogen receptor alpha expression level in uterine tissue cells by the climacterium.

<Example 3> Improvement Effect in Reduction of Uterine Tissue Estrogen Receptor Alpha Expression of Loganin in Female Climacteric Mouse Model An ordinary female climacteric symptom results in a remarkable reduction in estrogen receptors in uterine tissue cells due to estrogen decrease. The estrogen receptor is activated by estradiol (17β-estradiol, E2) and has two classes of estrogen receptor alpha and estrogen receptor beta. In the uterus, the estrogen receptor alpha plays a more important role than the estrogen receptor beta, and during climacterium, a marked reduction in the estrogen receptor alpha causes contraction and degeneration of the uterus. The mRNA expression level of the estrogen receptor alpha gene and the estrogen receptor alpha protein expression level by immunohistochemistry of section of the uterus were analyzed after 12 weeks of administration of Loganin to climacteric mouse model followed by extirpating uterus. When compared to normal Sham mouse without ovariectomy, the expression levels of the estrogen receptor alpha mRNA (FIG. 7a) and protein levels (FIG. 7b) were significantly decreased in ovariectomized OVX mouse. A comparison group of non-efficacious compound administration, $SrCl_2$ mouse has no difference with OVX mouse. However, the Loganin-administered group significantly inhibited the mRNA expression of the estrogen receptor alpha and the decrease of the estrogen receptor alpha protein (FIGS. 7a and 7b). Statistical analysis also showed significance of efficacy (*: $p<0.05$ vs. OVX negative control).

Figure 8A:
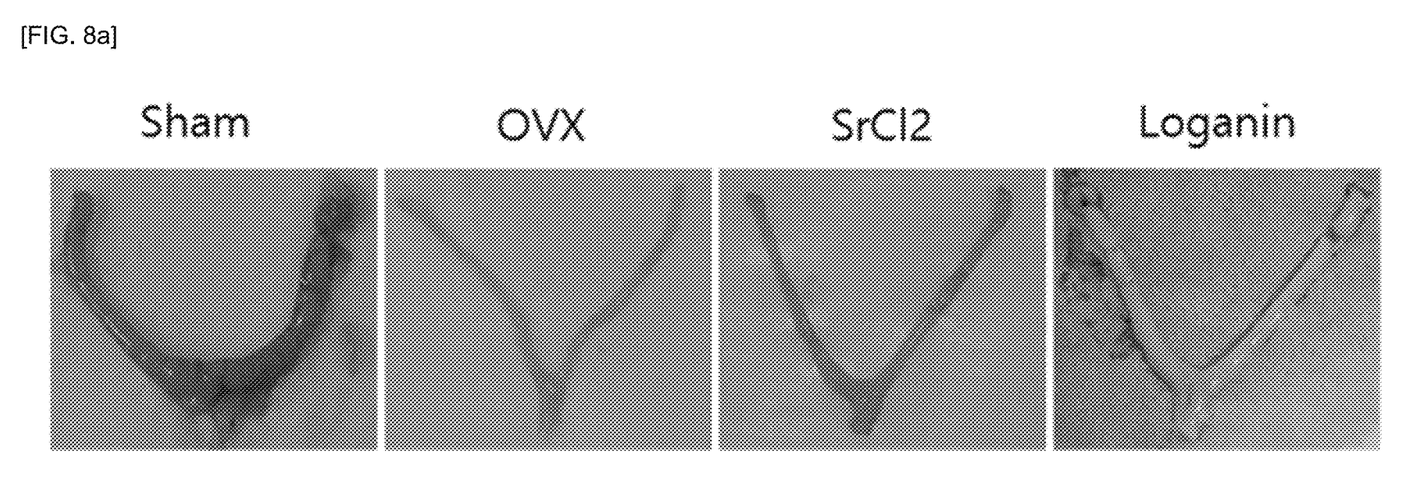
FIG. 8a shows the results of the uterus-extirpated mouse after 12 weeks of administration of Loganin of 10 mg/kg/day to climacteric mouse model, indicating that Loganin is significantly effective in inhibiting the contraction and degeneration by the climacterium.
Figure 8B:
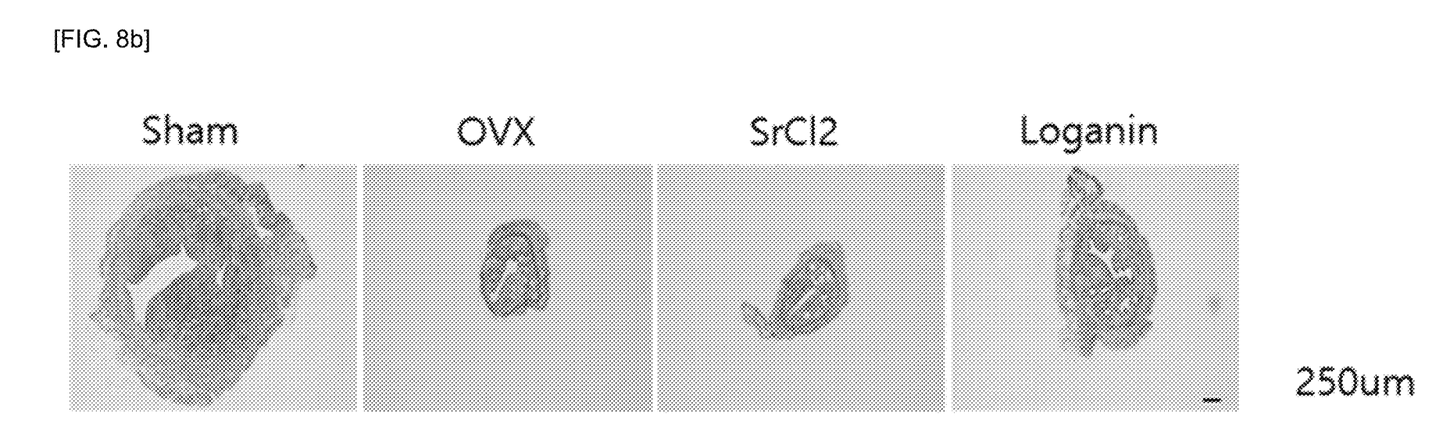
FIG. 8b shows the results of the H & E stained section of the uterus after 12 weeks of administration of Loganin of 10 mg/kg/day to climacteric mouse model, indicating that Loganin is significantly effective in inhibiting the contraction and degeneration by the climacterium.
Figure 8C:
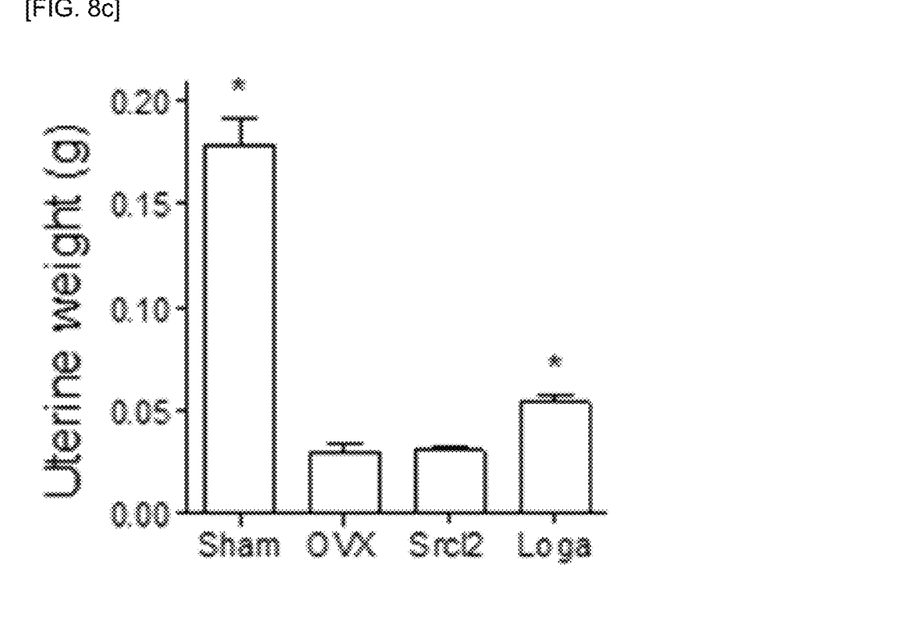
FIG. 8c shows the weight of the uterus after 12 weeks of administration of Loganin of 10 mg/kg/day to climacteric mouse model, indicating that Loganin is significantly effective in inhibiting the contraction and degeneration by the climacterium.

<Example 4> Improvement of Uterine Contraction and Degeneration of Loganin in Female Climacteric Mouse Model An ordinary female climacteric symptom results in uterine contraction and degeneration due to estrogen decrease. The shape, size, thickness and weight of the uterus were observed after 12 weeks of administration of Loganin to female climacteric mouse model followed by extirpating uterus. When compared to normal Sham mouse without ovariectomy, the uterus was small (FIG. 8a), the thickness of the section was thin (FIG. 8b) and the uterine weight was light (FIG. 8c) in ovariectomized OVX mouse. A comparison group of non-efficacious compound administration, $SrCl_2$ mouse has no difference with OVX mouse. However, the outward shape and size of the uterus, the thickness of the H & E-stained uterine section, and the weight thereof were significantly inhibited in the Loganin-administered group (FIGS. 8a, 8b and 8c). Statistical analysis also showed significance of efficacy (*: $p<0.05$ vs. OVX negative control).

Figure 9A:
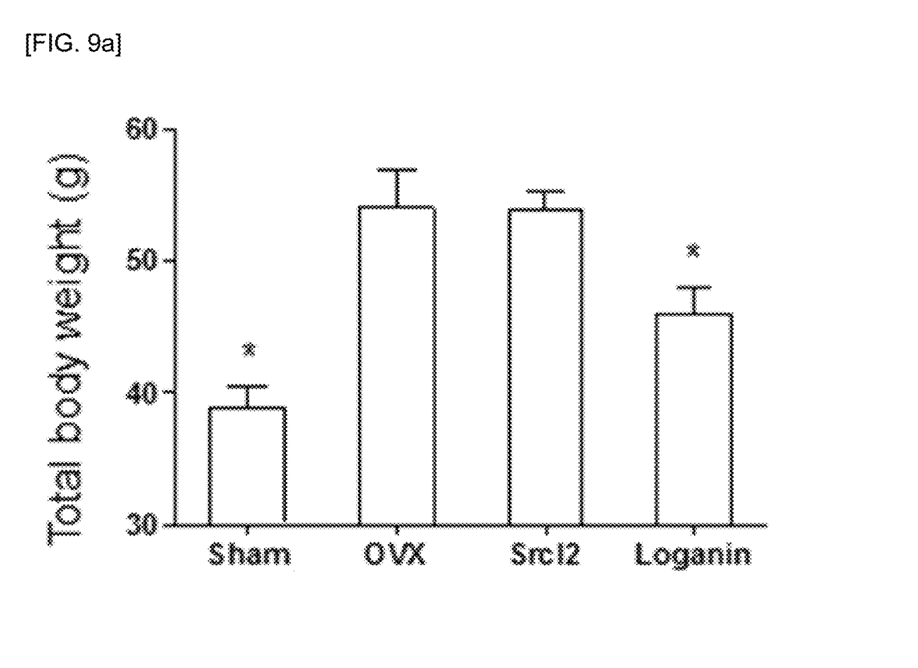
FIG. 9a shows the results of measuring the body weight of mouse which is hormone related to fat metabolism of serum separated from the mouse blood after 12 weeks of administration of Loganin of 10 mg/kg/day to climacteric mouse model, indicating that Loganin is significantly effective in inhibiting weight gain by the climacterium and increase in hormones related to fat metabolism.
Figure 9B:
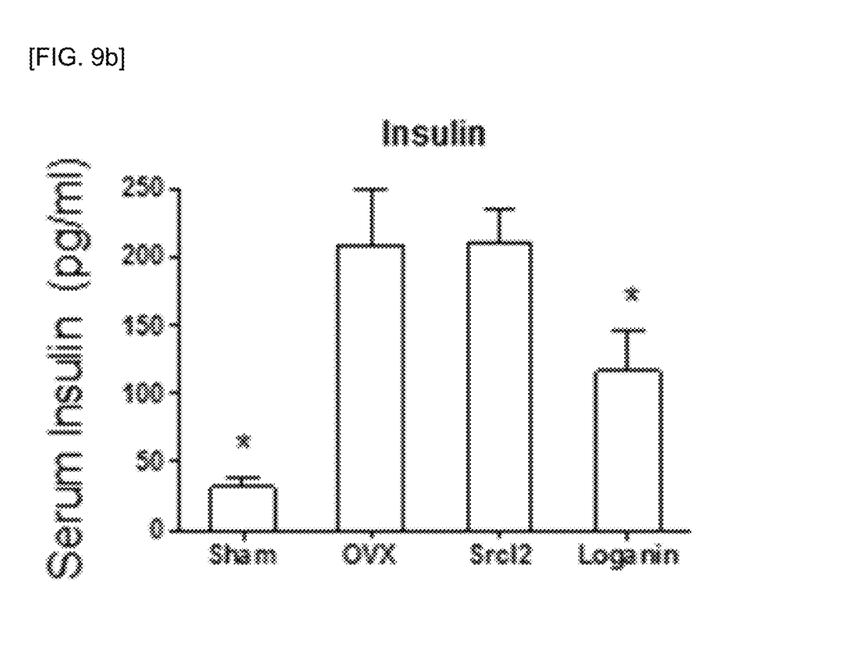
FIG. 9b shows the results of measuring the amount of insulin which is hormone related to fat metabolism of serum separated from the mouse blood after 12 weeks of administration of Loganin of 10 mg/kg/day to climacteric mouse model, indicating that Loganin is significantly effective in inhibiting weight gain by the climacterium and increase in hormones related to fat metabolism.
Figure 9C:
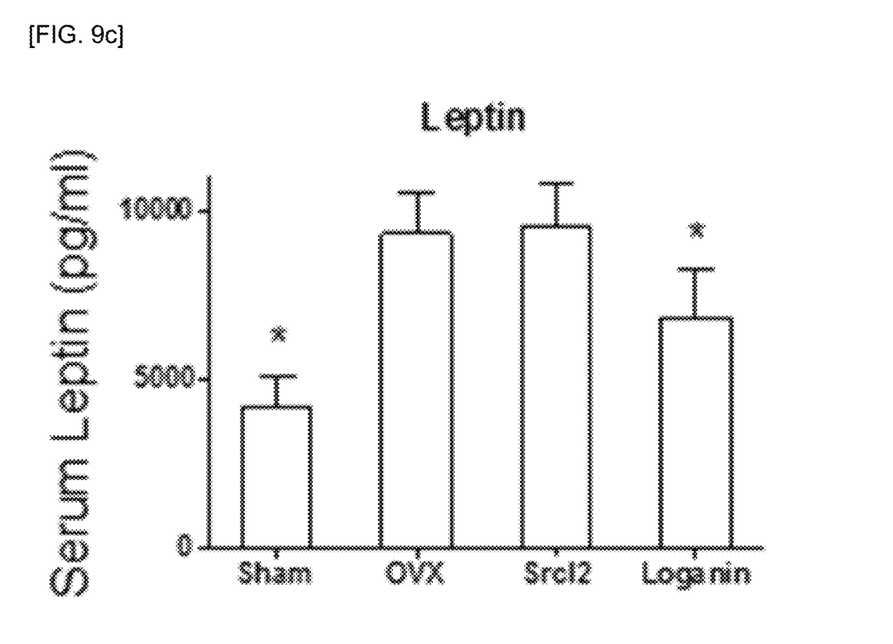
FIG. 9c shows the results of leptin which is hormone related to fat metabolism of serum separated from the mouse blood after 12 weeks of administration of Loganin of 10 mg/kg/day to climacteric mouse model, indicating that Loganin is significantly effective in inhibiting weight gain by the climacterium and increase in hormones related to fat metabolism.

<Example 5> Improvement Effect of Weight Gain of Loganin in Female Climacteric Mouse Model An ordinary female climacteric symptom results in weight gain due to estrogen decrease. The changes in body weight of mice and the presence of insulin and leptin, the metabolic hormone proteins, were measured by ELISA after 12 weeks of administration of Loganin to female climacteric mouse model. When compared to normal Sham mouse without ovariectomy, the body weight was significantly increased (FIG. 9a) and insulin (FIG. 9b) and leptin (FIG. 9c) were increased in ovariectomized OVX mouse. A comparison group of non-efficacious compound administration, $SrCl_2$ mouse has no difference with OVX mouse. However, the weight gain was significantly inhibited (FIG. 9a), and the increase in lipid metabolism-related hormones insulin and leptin were also significantly inhibited (FIGS. 9b and 9c) in the Loganin-administrated group. Statistical analysis also showed significance of efficacy (*: $p<0.05$ vs. OVX negative control).

Figure 10A:
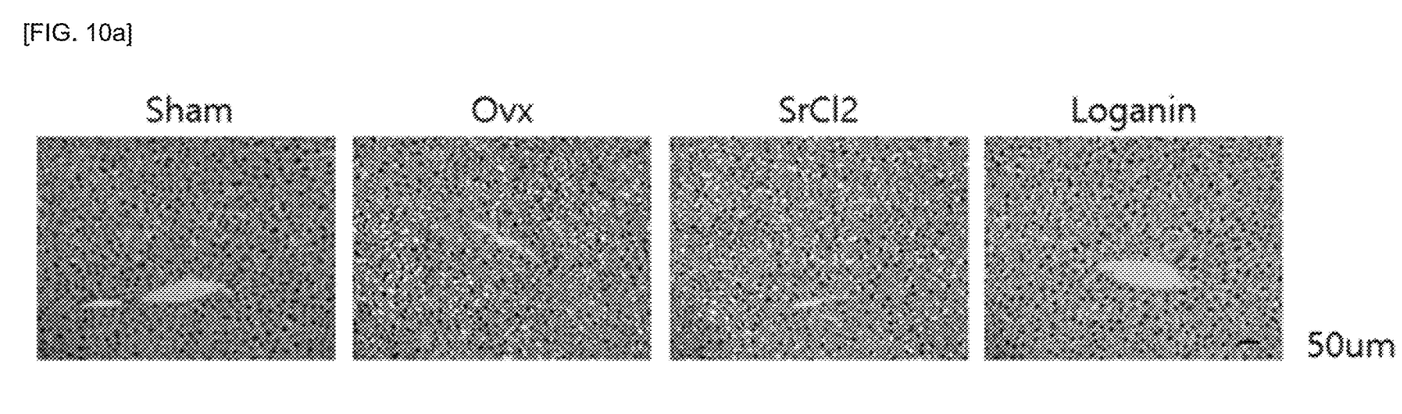
FIG. 10a shows the results of H & E staining of liver of mouse after 12 weeks of administration of Loganin of 10 mg/kg/day to climacteric mouse model followed by extirpating liver and abdominal adipose tissue, indicating that Loganin is significantly effective in inhibiting the accumulation of fat in the liver and the increase of fat cell size in the abdominal adipose tissue by the climacterium.
Figure 10B:
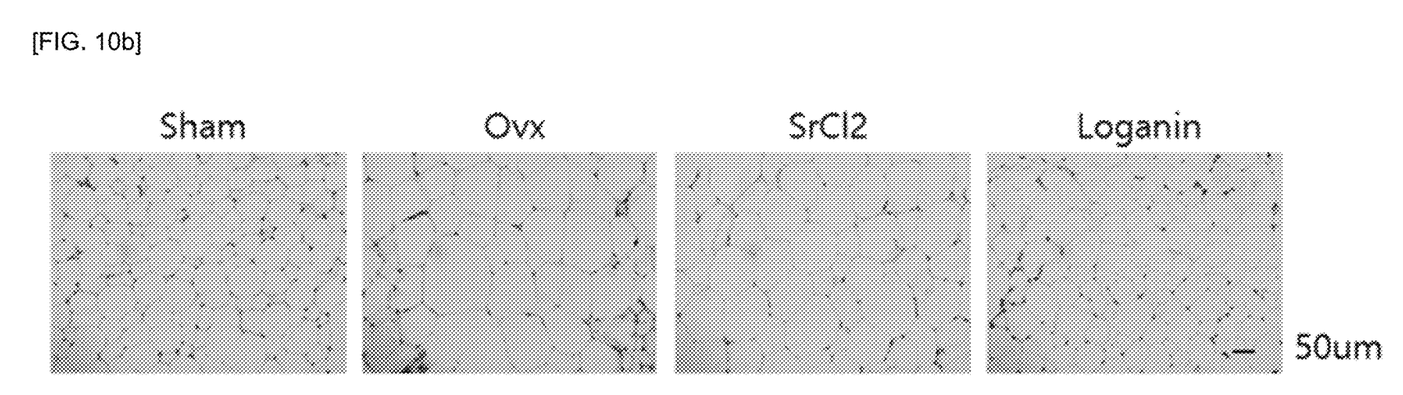
FIG. 10b shows the results of abdominal adipose tissue of mouse after 12 weeks of administration of Loganin of 10 mg/kg/day to climacteric mouse model followed by extirpating liver and abdominal adipose tissue, indicating that Loganin is significantly effective in inhibiting the accumulation of fat in the liver and the increase of fat cell size in the abdominal adipose tissue by the climacterium.

<Example 6> Improvement Effect of Fat Accumulation in Liver and Fat Cell Size Increase in Abdominal Adipose Tissue of Loganin in Female Climacteric Mouse Model In general, when estrogen is reduced in female climacterium, new estrogen is produced from adipocytes to offset the estrogen deficiency. In this process, more fat cells are produced and can cause abdominal obesity. In other words, fat accumulation in the liver and fat cell size increase in abdominal adipose tissue are caused by the increase of insulin and leptin, which are hormone proteins related to lipid metabolism. Liver and abdominal adipose tissues of mice were extirpated and H & E stained after 12 weeks of administration of Loganin to female climacteric mouse model. When compared to normal Sham mouse without ovariectomy, fat accumulation in the liver was significantly increased (FIG. 10a) and the size of fat cells of abdominal adipose tissue was markedly increased (FIG. 10b) in ovariectomized OVX mouse. A comparison group of non-efficacious compound administration, $SrCl_2$ mouse has no difference with OVX mouse. However, Loganin remarkably inhibited the fat accumulation in the liver and the increase in fat cell size in the abdominal adipose tissue by climacterium (FIGS. 10a and 10b) in the Loganin-administrated group.

The invention claimed is:

1. A method of ameliorating or treating hot flush caused by a decrease in estrogen secretion in a subject in need thereof, consisting of:
   administering a therapeutically effective amount of loganin or a pharmaceutically acceptable salt thereof as an active ingredient to the subject, wherein the hot flush caused by the decrease in estrogen secretion is ameliorated or treated.

2. A method of ameliorating or treating sweating caused by a decrease in estrogen secretion in a subject in need thereof, consisting of:
   administering a therapeutically effective amount of loganin or a pharmaceutically acceptable salt thereof as an active ingredient to the subject, wherein the sweating caused by the decrease in estrogen secretion is ameliorated or treated.

3. A method of ameliorating or treating vaginal atrophy caused by a decrease in estrogen secretion in a subject in need thereof, consisting of:
   administering a therapeutically effective amount of loganin or a pharmaceutically acceptable salt thereof as an active ingredient to the subject, wherein the vaginal atrophy caused by the decrease in estrogen secretion is ameliorated or treated.

4. A method of ameliorating or treating uterine atrophy caused by a decrease in estrogen secretion in a subject in need thereof, consisting of:
   administering a therapeutically effective amount of loganin or a pharmaceutically acceptable salt thereof as an active ingredient to the subject, wherein the uterine atrophy caused by the decrease in estrogen secretion is ameliorated or treated.

* * * * *